United States Patent
Deshpande et al.

(10) Patent No.: US 6,844,471 B2
(45) Date of Patent: Jan. 18, 2005

(54) METHOD FOR THE CONVERSION OF A Z-ISOMER INTO E-ISOMER

(75) Inventors: Pandurang Balwant Deshpande, Chennai (IN); Senthil Kumar Udayampalayam Palanisamy, Erode (IN); Gnanaprakasam Andrew, Chennai (IN)

(73) Assignee: Orchid Chemicals and Pharmaceuticals Limited, Tamilnadu (IN)

( * ) Notice: Subject to any disclaimer, the term of this patent is extended or adjusted under 35 U.S.C. 154(b) by 5 days.

(21) Appl. No.: 10/310,048

(22) Filed: Dec. 5, 2002

(65) Prior Publication Data

US 2004/0015020 A1 Jan. 22, 2004

(51) Int. Cl.[7] .............................................. C07C 39/12
(52) U.S. Cl. ........................ 568/729; 568/627; 568/646
(58) Field of Search ................................ 568/627, 646, 568/729

(56) References Cited

U.S. PATENT DOCUMENTS

| | | | | |
|---|---|---|---|---|
| 2,311,093 A | * | 2/1943 | Serini et al. | 568/729 |
| 2,346,049 A | * | 4/1944 | Rohrmann | 568/646 |
| 6,048,903 A | * | 4/2000 | Toppo | 514/733 |

FOREIGN PATENT DOCUMENTS

WO        WO01/60774        * 8/2001

OTHER PUBLICATIONS

Kim, J. Med.Chem., vol. 45, pp. 160–164 (Published on Web Dec. 7, 2001).*

* cited by examiner

Primary Examiner—Michael L. Shippen

(74) Attorney, Agent, or Firm—Oliff & Berridge, PLC

(57) ABSTRACT

A method of converting (Z)-1-(3,5-disubstituted phenyl)-2-(4-substituted phenyl)ethene of general formula (II) to (E)-1-(3,5-disubstituted phenyl)-2-(4-substituted phenyl)ethene of general formula (I)

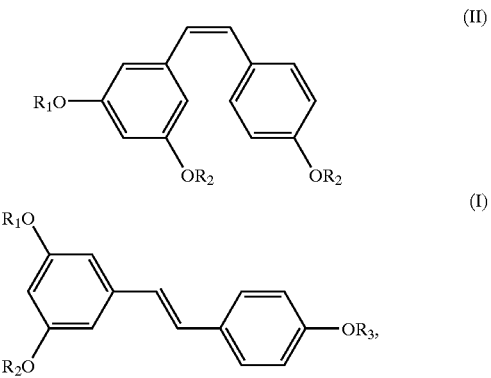

wherein $R_1$, $R_2$, and $R_3$ are the same or different and independently represent $(C_1-C_4)$alkyl, $(C_1-C_4)$alkoxy $(C_1-C_4)$alkyl, $(C_1-C_4)$alkoxy$(C_1-C_4)$alkoxy$(C_1-C_4)$alkyl, allyl, vinyl, silyl, formyl, acyl, aryl$(C_1-C_4)$alkyl or substituted aryl$(C_1-C_4)$alkyl group. The present invention also provides a process for the conversion of (E)-(3,5-disubstituted phenyl-2-(4-substituted phenyl)ethene of general formula (I) to E-resveratrol of formula (III).

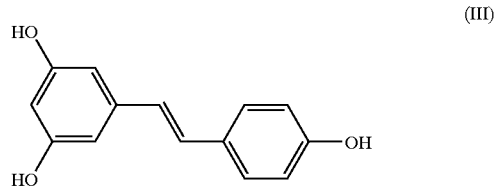

7 Claims, No Drawings

METHOD FOR THE CONVERSION OF A Z-ISOMER INTO E-ISOMER

FIELD OF THE INVENTION

The present invention relates to a method of converting (Z)-1-(3,5-disubstituted phenyl)-2-(4-substituted phenyl) ethene of general formula (II) to (E)-1-(3,5-disubstituted phenyl)-2-(4-substituted phenyl)ethene of general formula (I)

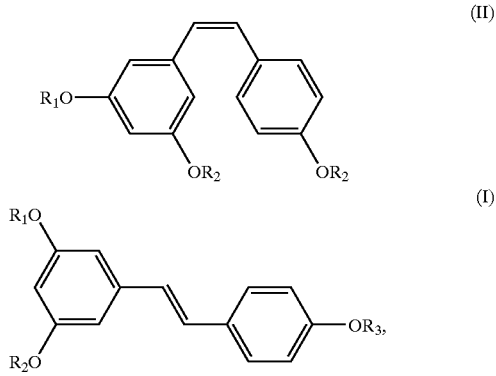

wherein $R_1$, $R_2$ and $R_3$ are same or different and independently represent $(C_1-C_4)$alkyl, $(C_1-C_4)$alkoxy$(C_1-C_4)$alkyl, $(C_1-C_4)$alkoxy$(C_1-C_4)$alkoxy$(C_1-C_4)$alkyl, allyl, vinyl, silyl, formyl, acyl, aryl$(C_1-C_4)$alkyl or substituted aryl $(C_1-C_4)$alkyl group.

The compound of formula (I) is useful as a key intermediate in the preparation of E-resveratrol of the formula (III), without contamination of the corresponding Z-isomer, which is formed during the process of synthesis. E-resveratrol has broad-spectrum biological activity. Moreover, the preparation of E-resveratrol can be accomplished quite easily and inexpensively.

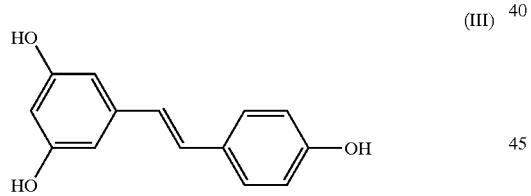

BACKGROUND OF THE INVENTION

In view of the vital biological activities of the polyhydroxylated trans-stilbenes, here have been a few methods reported for the synthesis of these compounds.

U.S. Pat. No. 6,048,903 describes the synthesis of E-resveratrol by the Wittig reaction of 3,5-dimethoxybenzyltriphenyl phosphonium salt with p-anisaldehyde in the presence of n-butyl lithium. In this method the mixture of Z- and E-olefins so obtained is demethylated with large amount of boron tribromide to get very low yield of the product. This method suffers from the low quality and use of expensive and hazardous reagents.

WO 00/21368 describes the condensation of phosphonate esters with aromatic aldehydes followed by demethylation using pyridine hydrochloride. In this method also the yields are low & the process is not commercially attractive.

Drewes, S. E.; Fletcher, I. P *J. Chem. Soc. Perkin Trans.* 1 1974, 961–962 & Bajaj, R.; Gill, M. T.; McLaughiln, J. L. *Rev. Latinoamer Quim.* 1987, 18, 79–80 reported the synthesis of analogs of E-resveratrol wherein a mixture of E- & Z-isomer is obtained.

Cunningham, J.; Haslam, E.; Haworth, R. D. *J. Chem. Soc.* 1963, 2875–2883 disclosed a different route, which comprises reaction of 3,5-dihydroxyphenylacetate and 3,4-dihydroxybenzaldehyde in acetic anhydride, decarboxylation of the ensuing 3,3',4,5'-tetraacetoxystilbene-α-carboxylic acid with copper and quinoline at high temperature, and hydrolysis of the resulting piceatannol tetraacetate with sodium hydroxide. The reported yields in these methods are moderate to low.

Ali, M. A.; Kondo, K.; Tsuda, Y. *Chem. Pharm. Bull.* 1992, 40(5) 1130–1136 described the Wittig reaction, wherein the undesired Z-isomers are reported to form to the extent of 52% along with the desired E-isomers (48%) when potassium tert-butoxide is employed.

Cushman, M.; Nagarathnam, D.; Gopal, D. et al. *J. Med. Chem.* 1992, 35 (12), 2293–2306; Chen, Yi-Ping; Lei, Tong-Kang. *Zhongguo Yiyao Gongye Zazhi* 2000, 31(7), 334–336 disclosed the formation of Z-isomers to the extent of 45% (E: 55%) when sodium hydride is used.

All of the above prior art disclosures have following limitations because of which the process is commercially not suitable and hazardous:

A mixture of Z- and E-isomers is always encountered and the isomers are separated by column chromatography or by crystallization techniques. Conversion of Z- into E-isomers with the aid of photochemical techniques are reported, wherein the mixture of Z- and E-isomers are irradiated with high powered lamps in the presence of catalysts like diaryl disulfides at high temperature.

In addition, the disulfides, which are essential for photochemical conversions, produce very bad smell and not environmentally acceptable.

Thus these techniques make the process not preferable for the industrial scale and, more over, these are non eco-friendly.

OBJECTIVES OF THE INVENTION

The objective of the present invention is to prepare exclusively the (E)-1-(3,5-disubstituted phenyl)-2-(4-substituted phenyl)ethene of general formula (I).

Another objective of the invention is to develop a simple, eco-friendly commercial method for converting Z-isomer of the formula (II) to the E-isomer of the formula (I).

Still another objective is to avoid the use of purification techniques like solvent crystallization & column chromatography.

Yet another objective of the present invention is to provide a simple and effective process without using photochemical reaction in the manufacturing process.

Still another objective of the present invention is to provide a high-yielding method of producing exclusively the E-resveratrol of the formula (III) from (E)-1-(3,5-disubstituted phenyl)-2-(4-substituted phenyl)ethene of general formula (I).

SUMMARY OF THE INVENTION

Accordingly, the present invention relates to a method of converting (Z)-1-(3,5-disubstituted phenyl)-2-(4-substituted phenyl)ethene of general formula (II) to (E)-1-(3,5-disubstituted phenyl)-2-(4-substituted phenyl)ethene of general formula (I)

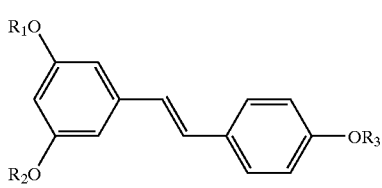

wherein $R_1$, $R_2$ and $R_3$ are same or different and independently represent $(C_1-C_4)$alkyl, $(C_1-C_4)$alkoxy$(C_1-C_4)$alkyl, $(C_1-C_4)$alkoxy$(C_1-C_4)$alkoxy$(C_1-C_4)$alkyl, allyl, vinyl, silyl, formyl, acyl, aryl$(C_1-C_4)$alkyl or substituted aryl $(C_1-C_4)$alkyl group, the said process comprising the steps of:

(a) treating an isomeric mixture of (Z)-1-(3,5-disubstituted phenyl)-2(4-substituted phenyl)ethene of the general formula (II) and (E)-1-(3,5-disubstituted phenyl)-2-(4-substituted phenyl)ethene of the general formula (I) or (Z)-1-(3,5-disubstituted phenyl)-2-(4-substituted phenyl)ethene of the general formula (II) with halogen in catalytic amounts, in an organic solvent for a period of 15 min to 16 hrs, at a temperature varying from −10° C. to +110° C., (b) quenching the resulting solution of step (a) into cold water and reducing the halogen using a reducing agent and (c) isolating the product formed in step (b) to produce (E)-1-(3,5-disubstituted phenyl)-2-(4-substituted phenyl)ethene of general formula (I).

DESCRIPTION OF THE INVENTION

In yet another embodiment of the present invention, there is provided a process for the conversion of (E)-1-(3,5-disubstituted phenyl)-2-(4-substituted phenyl)ethene of general formula (I) prepared by a process described above to E-resveratrol of the formula (III) which comprises deprotecting the protecting groups $R_1$, $R_2$, and $R_3$ by conventional methods.

In an embodiment of the present invention, the groups represented by $R_1$, $R_2$, and $R_3$ are selected from $(C_1-C_4)$ alkyl group such as methyl, ethyl, n-propyl, iso-propyl, n-butyl, iso-butyl, sec-butyl; $(C_1-C_4)$alkoxy$(C_1-C_4)$alkyl group such as methoxymethyl, methoxyethyl, methoxypropyl, ethoxymethyl, ethoxyethyl, ethoxypropyl; $(C_1-C_4)$alkoxy$(C_1-C_4)$alkoxy$(C_1-C_4)$alkyl group such as methoxyethoxymethyl, methoxyethoxyethyl; allyl, vinyl, silyl, formyl, acyl group such as acetyl, propanoyl, butanoyl or benzoyl; aryl$(C_1-C_4)$alkyl or substituted aryl$(C_1-C_4)$ alkyl group such as benzyl, phenethyl, diphenylmethyl, p-methoxybenzyl, p-nitrobenzyl, p-methylbenzyl or o-chlorobenzyl.

In yet another embodiment of the present invention, the solvents used in step (a) are selected from chloroform, dichloromethane, dioxane, THF, methanol, ethanol or iso-propanol and the like, preferably dichloromethane.

In another embodiment of the present invention, the stereochemical conversion is carried out at a temperature in the range of −10° C. to +110° C., and particularly, 0–40° C.

In still another embodiment of the present invention, the halogen used in step (a) is selected from iodine, chlorine or bromine, in catalytic quantities ranging from 0.1% w/w to 10% w/w, more particularly, from 1% w/w to 5% w/w.

In still another embodiment of the present invention, the reducing agent used in step (b) is selected from olefins like cyclohexene, cyclopentene, isoprene or inorganic reagents like sodium metabisulfite, sodium thiosulfate, sodium bisulfite and the like.

The foregoing technique has been found to be markedly attractive, both from commercial point of view, as well as from a stereo selectivity standpoint, and affords an almost exclusive formation of the E-isomer and is also free from the limitations discussed above.

The starting materials of the present invention, (Z) 1-(3,5-disubstituted phenyl)-2-(4-substituted phenyl)ethene of general formula (II) or its mixture with the corresponding E-isomer can be produced by the methods known in the art.

The probable mechanism of the stereochemical conversion is predicted in which a reversible addition-elimination of iodine to the double bond of the subject compound of the formula (II), which results in the formation of stable E-isomer exclusively has been suggested. The mechanism is shown in Scheme-1 below:

Scheme -1

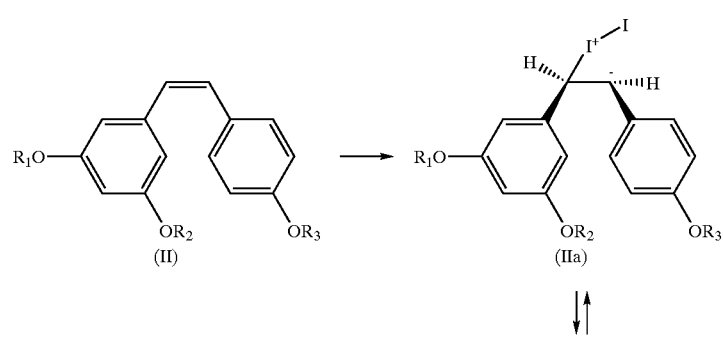

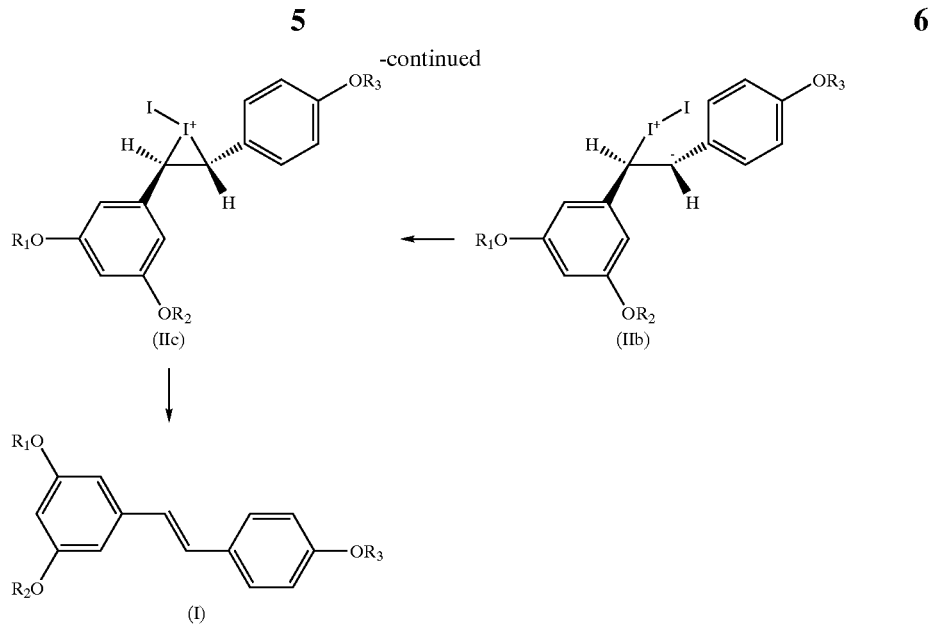

(IIc) (IIb)

(I)

The present invention is illustrated with the following examples, which should not be construed to limit the scope of the invention.

EXAMPLE 1

Preparation of (E)-1-(4-(benzyloxy)phenyl)-2-(3,5-bis(benzyloxy)phenyl)ethene (I)

A mixture of Z- and E-isomers, (Z)-1-(4-(benzyloxy)phenyl)-2-(3,5-bis(benzyloxy)phenyl)ethene and (E)-1-(4-(benzyloxy)phenyl)-2-(3,5-bis(benzyloxy)phenyl)ethene (25 gm) in an approximate ratio of 45%:55%, respectively, was dissolved in chloroform (200 ml). To the clear solution, iodine (1 gm) was added at 28–33° C. and maintained at this temperature for 12 hours. After the reaction was over, the reaction mixture was quenched with sodium thiosulphate, extracted into chloroform and the organic layer concentrated under vacuum. Treatment of the resulting residue, with methanol followed by filtration afforded (E-1-(4-(benzyloxy)phenyl)-2-(3,5-bis(benzyloxy)phenyl)ethene in quantitative yield and in exclusive E-form. M. pt. 156–158° C.; $^1$H NMR (CDCl$_3$, Bruker 400 MHz Avance): δ 5.09 (2, 4H), 5.11 (s, 2H), 6.56 (t, J=2.1 Hz), 6.77 (d, J=2.1 Hz, 2H), 6.91 (d, J=16.2 Hz, 1H), 6.99 (d, J=8.7 Hz, 2H), 7.04 (d, J=16.2 HZ, 1H), 7.34–7.48 (m, 17H); Mass m/e: 498.2. HPLC confirms that the Z-isomer content is <0.01%. (For HPLC analysis, the Z-isomer was produced and the stereochemistry confirmed by $^1$H NMR).

EXAMPLE 2

Preparation of (E)1-(3,5-dihydroxyphenyl)-2-(4-hydroxyphenyl)ethene of the formula (III):

Into a 3 lit. round-bottomed flask equipped with a thermometer were added aluminum chloride (390.35 gm) and N,N-dimethylaniline (413.10 gm) maintaining the temperature at 40–50° C. To this solution, a solution of (E)-1-(4-(benzyloxy)phenyl)-2-(3,5-bis(benzyloxy)phenyl)ethene (243 gm) prepared according to example 1 in dichloromethane was added and stirred well. After the reaction was over, the reaction mixture was acidified, extracted into ethyl acetate and concentrated to get pure (E)1-(3,5-dihydroxyphenyl)-2-(4-hydroxyphenyl)ethene (E-Resveratrol) in the exclusive E- form in 90% yield. $^1$H NMR (DMSO-d$_6$, Bruker 400 MHz Avarice): δ 6.11 (t, J=1.8 Hz), 6.38 (d, J=1.8 Hz, 2H), 6.75 (d, J=8.5 Hz, 2H), 6.82 (d, J=16.3 Hz, 1H), 6.92 (d, J=16.3 Hz), 7.39 (d, J=8.4 Hz, 2H); Mass m/e: 228.2.

What is claimed is:

1. A method of converting (Z)-1-(3,5-disubstituted phenyl)-2-(4-substituted phenyl)ethene of general formula (II) to (E)-1-(3,5-disubstituted phenyl)-2-(4-substituted phenyl)ethene of general formula (I)

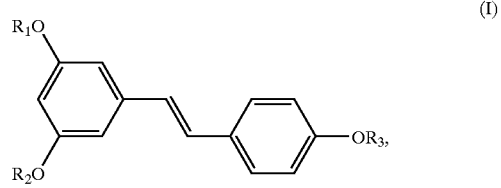

wherein $R_1$, $R_2$, and $R_3$ are the same or different and independently represent aryl($C_1$–$C_4$) alkyl group or substituted aryl($C_1$–$C_4$)alkyl group, the method comprising the steps of:

(a) treating an isomeric mixture of (Z)-1-(3,5-disubstituted phenyl)-2-(4-substituted phenyl)ethene of the general formula (II) and (E)-1-(3,5-disubstituted phenyl)-2-(4-substituted phenyl)ethene of the general formula (I) or (Z)-1-(3,5-disubstituted phenyl)-2-(4-substituted phenyl)ethene of the general formula (II)

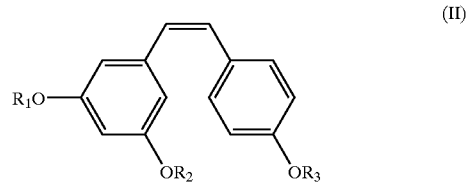

with a halogen in catalytic amounts, in an organic solvent for a period of 15 min to 16 hrs, at a temperature ranging from −10° C. to +110° C.;

(b) quenching the resulting solution of step (a) in water and reducing the halogen using a reducing agent; and (c) isolating the product formed in step (b) to produce (E)1-(3,5-disubstituted phenyl)-2-(4-substituted phenyl)ethene of general formula (I).

2. The method according to claim 1, wherein the groups represented by $R_1$, $R_2$, and $R_3$ are benzyl, phenethyl, diphenylmethyl, p-methoxybenzyl, p-nitrobenzyl, p-methylbenzyl, or o-chlorobenzyl.

3. The method according to claim 1, wherein the solvent used in step (a) is selected from the group consisting of chloroform, dichloromethane, dioxane, THF, methanol, ethanol, and isopropanol.

4. The method according to claim 1, wherein the stereochemical conversion is carried out at a temperature in the range of 0–40° C.

5. The method according to claim 1, wherein the halogen in step (a) is iodine, chlorine, or bromine, in catalytic quantities ranging from 0.1% w/w to 10% w/w.

6. The method according to claim 1, wherein the reducing agent used in step (b) is selected from the group consisting of cyclohexene, cyclopentene, sodium metabisulfite, sodium thiosulfate, and sodium bisulfite.

7. The process according to claim 1, further comprising converting the compound of general formula (I) obtained in step (c) into E-resveratrol of formula (III) by deprotecting the protecting groups

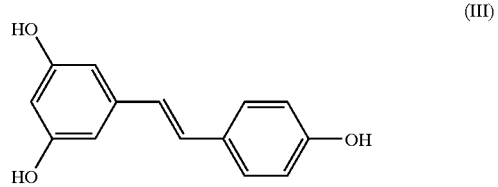

(III)

* * * * *